(12) United States Patent
Du (10) Patent No.: US 7,167,774 B2
(45) Date of Patent: Jan. 23, 2007

(54) COMPUTER-GUIDED SAMPLE HANDLING (76) Inventor: Ping Du, 6 Santa Luzia Aisle, Irvine, CA (US) 92606

( * ) Notice: Subject to any disclaimer, the term of this patent is extended or adjusted under 35 U.S.C. 154(b) by 209 days.

(21) Appl. No.: 10/983,454

(22) Filed: Nov. 6, 2004

(65) Prior Publication Data
US 2005/0102056 A1 May 12, 2005

Related U.S. Application Data (60) Provisional application No. 60/518,538, filed on Nov. 7, 2003.

(51) Int. Cl.
*G06F 7/00* (2006.01)
(52) U.S. Cl. ................................. 700/213
(58) Field of Classification Search .............. 700/213
See application file for complete search history.

(56) References Cited

U.S. PATENT DOCUMENTS 6,991,713 B2 * 1/2006 Adourian et al. ........... 204/453
7,064,318 B2 * 6/2006 Bui ........................... 250/282

* cited by examiner

*Primary Examiner*—Khoi H. Tran (57) ABSTRACT

A device for sample handling directly illuminates the sample in sample compartment 36 with its corresponding image 22 on display panel 18. The device contains a sample tray 30, a computer 10 installed with custom software, and a visual display panel 18. The device supports defining, testing, and executing a sample handling protocol with high accuracy, efficiency, and flexibility. The device is also portable and inexpensive to build. A user can transfer samples from source locations to destination locations under the guidance of this device without memorizing the protocol or reading instructions on a printed material. A user can also record data for certain characteristics of samples under the guidance of this device. With the invented device, the risk of locating a wrong sample or placing a sample at a wrong location can be minimized and sample handling operations become more efficient and less stressful.

12 Claims, 5 Drawing Sheets
(1 of 5 Drawing Sheet(s) Filed in Color)

COMPUTER-GUIDED SAMPLE HANDLING

CROSS-REFERENCE TO RELATED APPLICATION(S)

This application claims the priority of U.S. Provisional Patent Application No. 60/518,538 filed on Nov. 7, 2003 entitled COMPUTER-GUIDED SAMPL HANDLING, the whole of which is herebyy incorporated by reference herein.

FEDERALLY SPONSORED RESEARCH

Not applicable.

SEQUENCE LISTING OR PROGRAM

Not applicable.

BACKGROUND OF THE INVENTION—FIELD OF INVENTION

This invention relates to a device for guiding sample handling, specifically to a device which is used for indicating locations of samples to be handled by computer generated visual effects.

BACKGROUND OF THE INVENTION

Sample handling refers to the movement and manipulation of samples or specimens, a common task performed in almost all laboratory research, such as pharmaceutical drug discovery, clinical testing, environmental analysis, and scientific education.

Sample handling in the laboratories are carried out in either manual or automated fashion. Manual operations are performed, typically without computerized guidance, by using a hand-held pipette if the sample is liquid, or by hand if the sample is in a removable container such as a vial. Robotic systems are available for automatically handling large number of samples according to predefined protocols. In recent years robotic systems have been widely used for liquid handling in combinatorial library synthesis, high-throughput screening, and sample management. Although these systems can provide high-throughput sample handling, they are typically complex, expensive, large in size, and not portable.

Due to the limitations of the robotic systems, scientists and technicians routinely perform manual sample handling for lower throughput tasks without using robotic systems. To reduce errors, some follow a sketched diagram or printed instructions of a protocol. However, when sample containers with non-trivial number of samples, such as 24, 48, 96, or 384-well micro titer plates, are used, the chance of incorrectly locating samples in a manual process becomes a major concern, especially in expensive and critical experiments. Manual sample handling remains tedious, stressful, and error-prone. In addition, the operational details of manual sample handling are often not recorded, making subsequent error checking difficult or impossible.

Thus, there is a strong need for a flexible, inexpensive, and easy-to-use technology for guiding manual sample handling in the laboratory. This invention describes a computerized device developed to guide the transfer of experimental samples. The goal is to provide the user with a flexible and robust mechanism to execute predefined experimental protocols with increased efficiency and accuracy.

BACKGROUND OF INVENTION—OBJECTS AND ADVANTAGES

The objects and advantages of the present invention are:

(a) to provide a device which through illumination points to or highlights samples to be handled in a step of a sample handling procedure;

(b) to provide a device which displays graphic and text guidance for specific sample handling actions in a step-by-step fashion;

(c) to provide a device which allows a user to handle samples without memorizing or reading instructions of a protocol;

(d) to provide a device which permits a user to define and store sample handling protocol;

(e) to provide a device which allows a user to modify and test sample handling protocol;

(f) to provide a device which facilitates automatic recording sample handling details, such as amount transferred and the time of transfer;

(g) to provide a device which can be used as a teaching aid to show sample handling actions of a protocol;

(h) to provide a device which facilitates convenient data recording of sample characteristics.

SUMMARY

In accordance with the present invention a device comprises a computer, an illumination apparatus, and a platform to accommodate positioning samples.

DRAWINGS—FIGURES

The patent or application file contains at least one drawing executed in color. Copies of this patent or patent application publication with color drawing(s) will be provided by the Office upon request and payment of the necessary fee.

DRAWINGS—REFERENCE NUMERALS 10 computer system
12 mouse
14 keyboard
16 cable
18 display panel
20 control menu and text box
24 image of sample compartment
26 image of sample container
28 alignment feature
30 sample tray
32 positioning feature
36 sample compartment
38 sample container
40 sample container images with adjustable formats (Plates)
41 sample container image with fixed format (Vial Rack)

44 projector
46 light beam

DETAILED DESCRIPTION—FIG. 1A–1C—PREFERRED EMBODIMENT

Figure 1A:
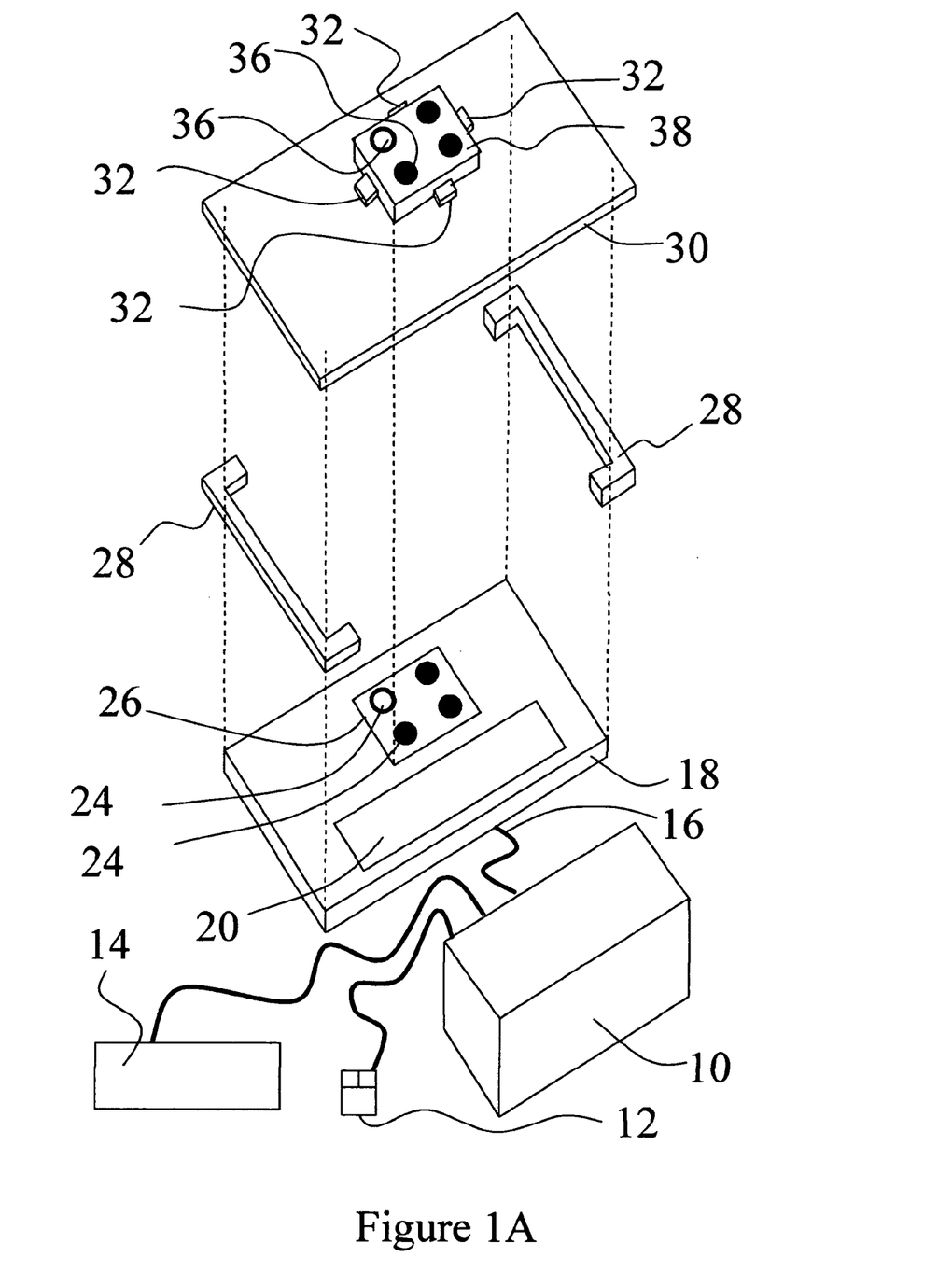
FIG. 1A shows the aspects of the preferred embodiment of a device for computer guided sample handling.

FIG. 1A shows a perspective view of the preferred embodiment of the device for sample handling of the present invention. The device has a computer system 10 preferably including a keyboard 14 and a mouse 12 as input devices. Display panel 18 is a device that can display texts and images. The display panel is connected to the computer system through cable 16. Suitable display panels include regular computer monitors such as Liquid Crystal Display (LCD) flat panel monitors, Cathode Ray Tube (CRT) monitors, and various television (TV) monitors. The effective display area is typically in a rectangular shape. A typical 15-inch LCD flat panel monitor has a flat and rectangular display area of 9 inches by 12 inches.

Sample tray 30 is used to hold sample containers. It is constructed with a sheet of rigid material in rectangular shape and about ⅛ inch in *thickness*, and has overall dimensions roughly 3 inches longer and 2 inches wider than the sides of the rectangle of the display panel's effective display area. For a 15-inch LCD flat panel monitor, the dimensions of the tray are roughly ⅛ inch in *thickness*, 11 inches in width, and 15 inches in length. The sample tray is made of transparent material, such as Lucite CP acrylic sheet. Alignment feature 28 is attached to the underside of tray 30 in such a way that the tray is aligned with display panel 18 when the tray is placed on the top of the display panel in a parallel fashion. In addition, positioning feature 32 is attached to tray 30 on the top side of the tray. The positioning feature 32 keeps the sample container 38 at specified position. Methods of attaching the alignment feature 28 and positioning feature 32 to sample tray 30 include gluing with an adhesive.

Sample container 38 may have at least one sample compartment 36. Each sample compartment may store one sample. In a 96-well micro titer plate, for example, the plate is the container and each well is a sample compartment. The top view image 24 of the sample container 38 is displayed on the display panel 18. There can be a plurality of containers and their respective images. The sample containers on the sample tray are superimposed over their corresponding images on the display panel. A portion of the display area 20 of the display panel is dedicated to control menu and text box for showing function buttons and text instructions. The contents on the display panel are displayed under the control of the software of the system. The location of the sample to be handled in a specific step is indicated by illuminating a sample container with its corresponding image on the display panel. In addition, the sample handling instructions corresponding to this step are also displayed on the panel. Thus, the invented device can provide on-demand visual location indication and text instructions in a step-by-step fashion under the computer guidance.

Figure 1B:
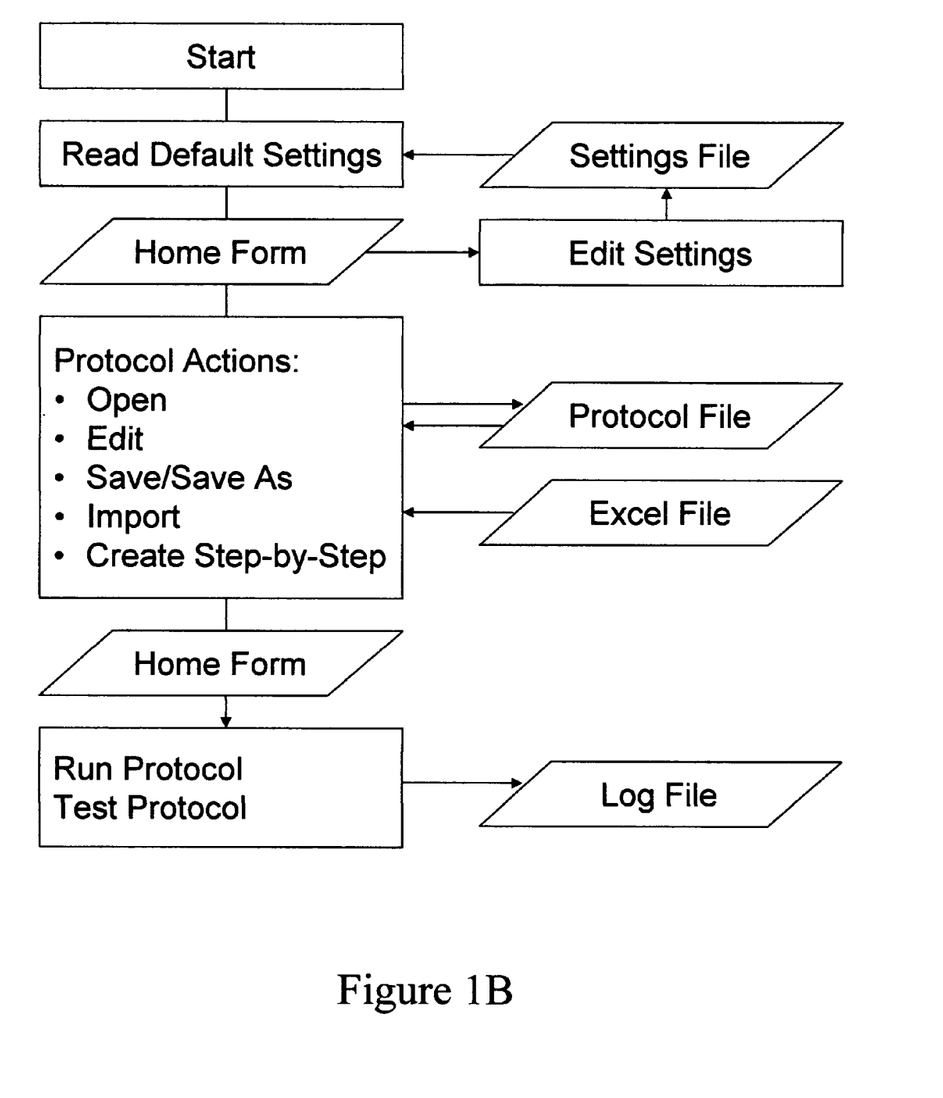
FIG. 1B shows the flowchart of a preferred software embodiment.

FIG. 1B shows the flow diagram of a preferred software embodiment The software is designed to execute a sample handling protocol, which is a series of sample handling steps linked together in a predetermined order. A protocol may include one or more standard micro titer plates as sample containers. It may use vials or external containers. External containers are large containers, such as solvent bottles, that do not fit on the sample tray. If more than four plates are used, the steps are grouped into tasks, with each task having four or less plates that can be mounted to the sample tray simultaneously. The user is instructed to change plates between tasks during protocol execution.

The preferred software embodiment includes functions for opening, editing, saving, importing, and creating a protocol. After a protocol is loaded, it may be tested or executed, as shown in the flow diagram in FIG. 1B.

At the start of the program, default settings such as plate format, well color and size, and highlight color and flash rate are read from a settings file in XML format. Users may adjust these configuration parameters and save them back to the settings file.

The user may open an existing protocol, or create a new protocol by either importing from an Excel file through the "Import" function or defining the protocol step by step within the application through the "Create Step-by-Step" function. When importing from Excel, the minimal information required in the Excel file is source well location. Other information such as destination wells, plate format, and transfer volume can also be specified in the Excel file. If no destination wells are specified, the samples are mapped systematically by row or column, as determined by the user. The system tracks the number of plates imported and breaks them down to tasks, with each task performing operations on a set of four or less plates. Multiple wells may be specified for a step, signaling multiple samples need to be handled in a single step, often by using a multi-channel pipette. External containers may be included. At rum time, use of external containers is indicated in the text instructions shown on the display panel.

The "Test Protocol" function runs through the steps of the protocol continuously without waiting for the user to signal the completion of the physical operations. The user may also use this function to review and validate a protocol, or to demonstrate a protocol for educational or training purposes.

The "Execute Protocol" function is used to carry out physical operations as instructed by the protocol. During execution, sample container images are generated on the display panel as signals to guide the user to execute individual operations, such as taking a sample from a source well and dispensing it into a destination well. For example, flashing a well in red indicates the location to take a sample; flashing another well in green indicates the location to dispense the sample. Details of the sample handling step and related information, such as amount to transfer, are displayed in a text box. Upon the completion of sample handling for the current step, the user signals to the system by stepping on a footswitch or hitting space bar of the keyboard. The relevant information of this completed step, such as time of execution and notes from the user, is saved in a log file.

Figure 1C:
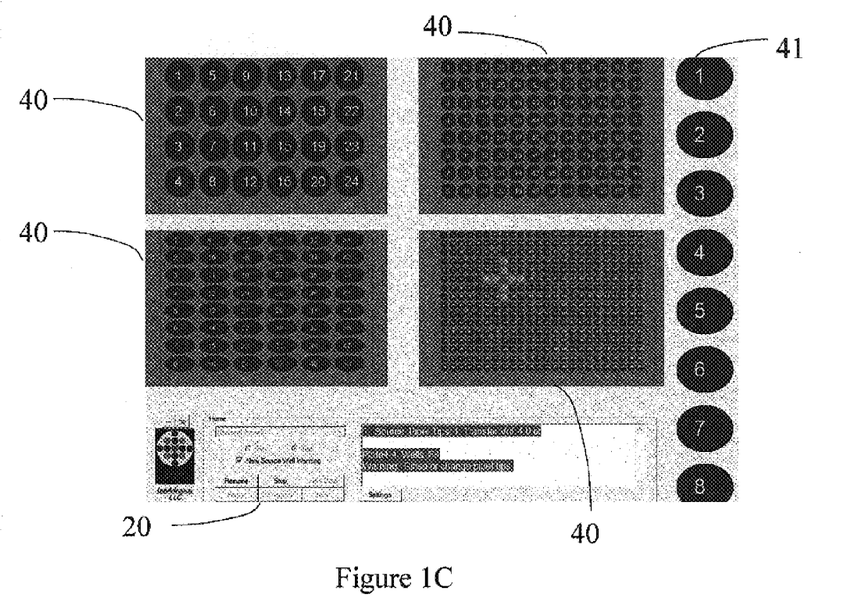
FIG. 1C shows the graphical user interface in the display panel.

FIG. 1C shows the graphical user interface on the sample display panel. Plates 40 is flexible in format (24-well, 48-well, 96-well, or 384-well), and reagent rack 41 is fixed in format with 8 sample compartments. The control menu 20 at the bottom of the panel provides functions for opening, editing, and saving a protocol, importing a protocol from Excel sheet, creating a protocol step-by-step, testing and executing a protocol. The user may edit and save software parameters through this control menu. During execution, details of the step are displayed in the text box.

DETAILED DESCRIPTION—FIG. 2 ALTERNATIVE EMBODIMENT

Figure 2:
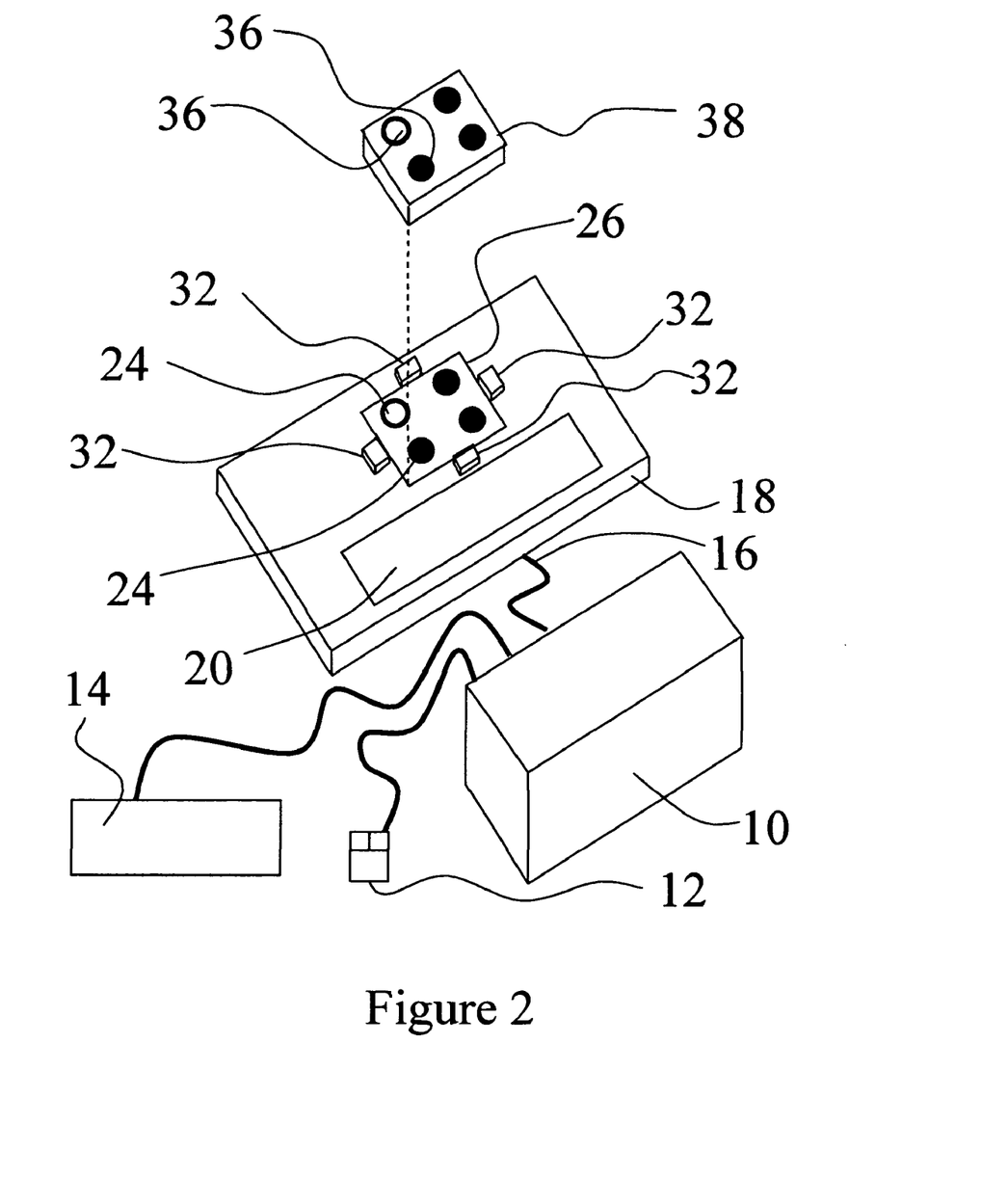
FIG. 2 shows an alternative embodiment without the sample tray.

FIG. 2 shows an alternative embodiment. The sample container 38 is directly placed on the display panel, assuming the display panel is strong enough to support the containers. Sample container positioning features 32, if desired, are installed on the surface of the display panel. The distance between the images on the display panel and the sample container is minimized and illumination of sample containers is thus improved. The software component of the alternative embodiment is identical to that of the preferred embodiment.

DETAILED DESCRIPTION—FIG. 3 ALTERNATIVE EMBODIMENT

Figure 3:
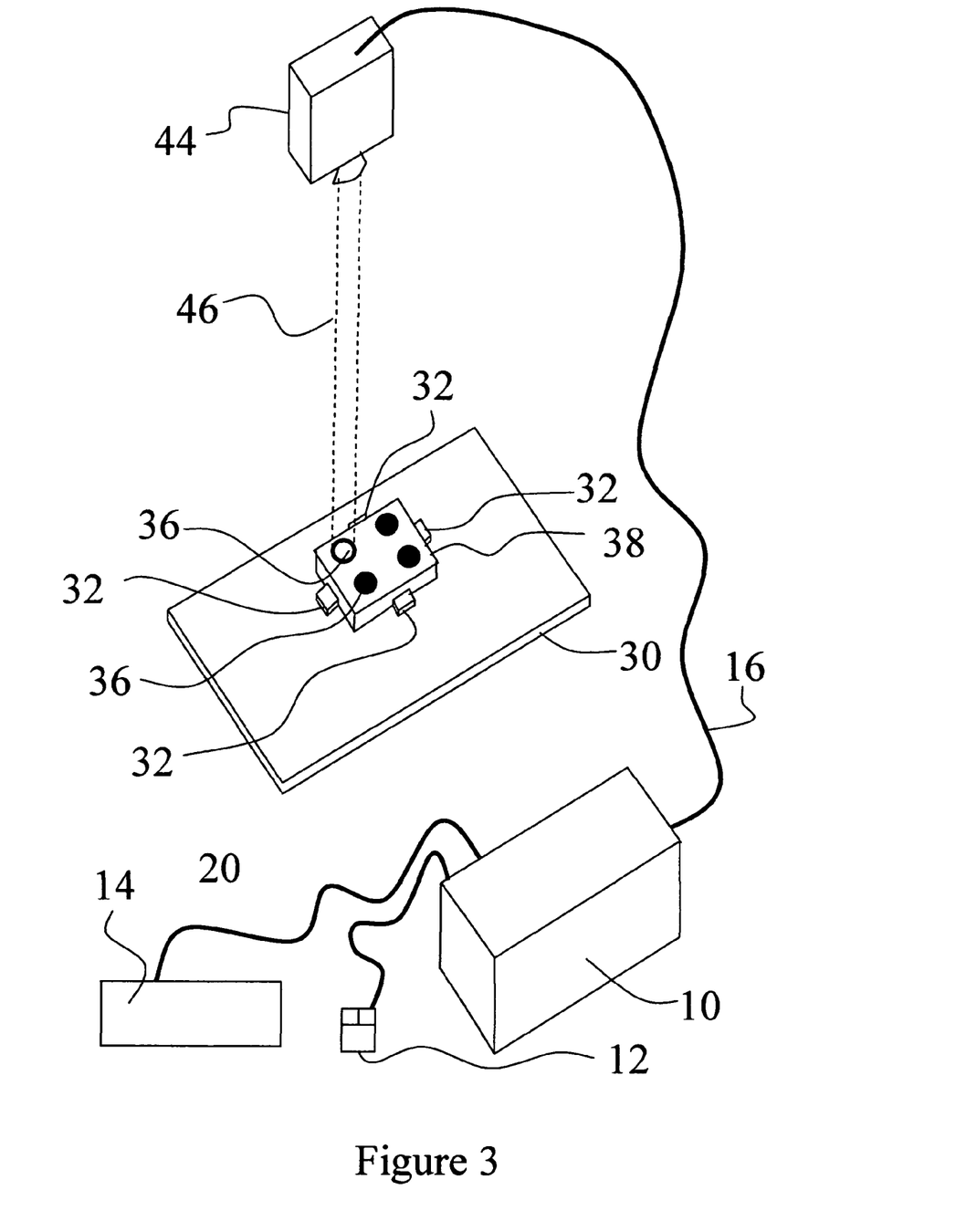
FIG. 3 shows an alternative embodiment a device for computer guided sample handling with a projector as illumination apparatus.

FIG. 3 shows another alternative embodiment with a projector as the illumination apparatus. Projector 44 is connected to a computer to generate desired images. Instead of illuminating samples by images on the display panel as in the preferred embodiment, light beam 46 points to samples. Projector 44 may be located on the same side of the sample container 38 relative to sample tray 30, as shown in FIG. 3, or on the opposite side of the sample container 38 relative to sample tray 30. If projector is on the same side as the sample containers, transparency of sample tray 30 and sample container 38 is not required. The software component of the alternative embodiment is identical to that of the preferred embodiment.

OPERATION—FIG. 1A–1C

The manner of using the invented device for sample handling includes following procedures:

(a) Adjust Setting Parameters

The system is configured with a default set of parameters for container format, size, position, well colors, flash highlight colors for source and destination wells, flash rate, etc, which are read in when the software is launched. The user may adjust these parameters to suit the needs of a particular protocol.

(b) Create a Protocol

A protocol may be created by importing from an Excel file or step-by-step using the graphical user interface. If a protocol has been created previously, it may be opened by using the "Open Protocol" function.

(c) Test Protocol

Once loaded, a protocol may be tested. Testing the protocol allows the user to review each step of the protocol without performing physical operations. If errors are found, they can be corrected. Testing a protocol also provides a means for protocol demonstrations for educational purposes.

(d) Execute Protocol

At the beginning of executing a protocol, the system instructs the user how many plates and vials to load to the display panel. The formats of the plates are shown in the plate images and text instruction box. At each step, the wells involved are highlighted with flashing colors. In the example shown in FIG. 1C, well F8 in the fourth plate is highlighted in red, signaling the user to move a sample from this location. Adjacent wells are also highlighted to help the user to locate the well. The details of the step, including transfer volume, are displayed in a text box. The user performs the physical operations of the step guided by the highlighted wells and the text display. After completion of the physical operations, the user signals to the system via an input device such as a mouse, a keyboard, or a footswitch. The system then moves to the next step. The system instructs the user to replace plates or vials if new plates and vials are needed for the next task.

EXAMPLE APPLICATIONS

The invented device is a general purpose guiding system for sample handling. It may be used for any laboratory tasks where liquid or vials need to be moved between plate wells, or between plate wheels and other containers. Below is a list of selected applications of the device.

(a) Parallel Chemical Synthesis

The invented device for sample handling helps executing parallel synthesis tasks, such as reagent dissolution and addition to the synthetic vessels. After the completion of synthesis, it guides the transfer of products to analytical plates for quality control and to storage plates for further distribution. Focused libraries and diversity oriented synthesis for lead optimization typically include tens or a few hundred compounds. The invented device is well suited for manual parallel synthesis of such compound collections. Creating a typical parallel synthesis protocol involves the following stages:

(1) Planning

This stage determines the number of reactions, number of reagents and reagent concentration, the number of products, the scale or targeted molar amount of each product and the layout of the reaction vessels. The planning can be performed in an Excel sheet, which is subsequently imported to software for the device. Excel templates for commonly used parallel synthesis formats, such as 4 by 6, 8 by 8, and 8 by 12, are distributed with the software package, and can be modified to suit the specific needs of the user.

(2) Reagent Weighing

The user weighs appropriate amounts of reagents based on the plan. The actual weight of each reagent can be updated in the planning Excel sheet, which includes information such as reagent ID and molecular weight. If the reagents are weighed into vials in a rack format, the Excel sheet may also contain rack ID and well location for each reagent.

(3) Reagent Dissolution

Once reagents are weighed into vials, solvent is added under the guidance of the invented device. Since the Excel sheet now contains actual weight and molecular weight of each reagent, the volume of the solvent to be added to each vial can be calculated. The invented device highlights the vial to add solvent and displays which solvent and how much to add.

(4) Reagent Transfer

Under the guidance of the SHOW system, the reagent solution is transferred from vials to wells in reaction blocks according to the layout information in the planning Excel sheet. The volume of transfer is determined by the synthesis scale planned and the chemical equivalence of the reagent relative to the final product. For multi-step reactions, the reagent weighing, dissolution, and addition steps are repeated according to the plan.

(b) Biological Assays

Biological assays require addition of buffers, reagents, dilution solvent, sample solutions, and control solutions to the wells of a plate. The invented device can be used to guide such liquid additions. Serial dilution is a simple and common procedure in biological assays, but a single pipetting positioning error can ruin the whole assay. The invented device provide precise pipetting positioning indication for serial dilution, which is particularly valuable for assays using higher density plate, such as 384-well plates.

In some biological assay experiments, the results can be determined visually with the assistance of the invented device. For example, in minimal bacterial inhibition concentration (MIC) assays, the assay plate is prepared by serial dilution of a chemical compound that inhibits bacterial growth. Bacteria are then added to the wells of the plate. Bacteria may grow in wells with lower concentrations of the compound, but may not grow in wells with higher concentration of the compound. After visually inspecting the growth of bacteria in the serially diluted samples one may easily record the sample with the lowest compound concentration that inhibits bacteria growth by simply clicking on the corresponding well. The MIC value is then automatically recorded.

(b) Sample Management

There are many tasks in sample management, including compound plating, picking compounds based on certain properties (cherry-picking), and vial sorting. All of these tasks can be assisted by the invented device.

(1) Compound Plating

Compound plating may occur for many reasons. One reason is to transfer synthetic products to storage and analytical plates after the completion of synthesis. This procedure involves transferring certain amount of the product to multiple plates, one for storage and one for analysis. If the formats of the analytical and storage plates are different from the synthetic plate, the mapping pattern information is required. Such mapping may be created in an Excel sheet with well to well level detail, or entered manually. When the protocol is executed, the invented device produces graphical highlighting of source and destination wells and the volume of transfer for each sample.

(2) Cherry-Picking

The invented device assists in picking specific samples in plates and transferring it to a destination plate. Cherry-picking may occur for many reasons, such as biological assay activity, compound purity, or amount.

Typically, the samples to be picked are specified in an Excel file. The file can be imported and the source wells are systematically mapped to the destination plates. When the protocol is executed, the source and destination wells are highlighted. Up to three source plates and one destination plate may be mounted on the sample tray. When all three source plates are picked, or when the destination plate is full, the system instructs the user to load new plates.

(3) Sample Sorting

The invented device provides an easy way for the user to sort samples from source plates to destination plates based on a given criterion, such as purity, amount, or activity. Cherry-picking discussed above is a special sample sorting, typically moving desired samples from multiple source plates to one destination plate. Sample sorting allows samples to be sorted into groups according to the source well to destination well mapping specified in an Excel sheet.

(d) Data Recording

As already discussed above in the example of the MIC assay, the invented device can be used to record sample characteristics. Sample characteristics obtained through visual inspection for a sample can be recorded conveniently by clicking on the corresponding sample compartment image. Additional information worth recording can also be recorded through keyboard input and automatically associated with the sample.

(e) Method Development and Training

The invented system can be used to test experimental protocols virtually to assist in the development of methods. It can also be used to demonstrate research procedures in a teaching or training environment, where a protocol is displayed step-by-step graphically.

Advantages

From the description above, a number of advantages of the invented device for computer-guided sample handling become evident:

(a) A user can perform sample handling by effortlessly following the instructions on the display panel, minimizing operation errors.

(b) A user can perform sample handling without memorizing or reading printed instructions of a protocol. Thus the sample handling will be more accurate, more efficiently, and less stressful compared to sample handling without on-demand step-by-step computer guidance.

(c) Details of sample handling operation are recorded automatically.

(d) Sample handling actions of a protocol can be demonstrated visually, which is helpful for reviewing the sample handling procedures and training users.

(e) Recording data for certain sample characteristics is made more efficient and less error-prone than typical manual approach in which a user first inspects samples then enters the finding on a notebook or into an electronic device, such as a computer.

(f) The device can be built inexpensively.

(g) The device is portable.

(h) The device is flexible and can be used in a wide range of application

CONCLUSION, RAMIFICATIONS, AND SCOPE

Although the description above contains many specifics, these specific should not be construed as limiting the scope of the invention but as merely providing illustrations of some of the presently preferred embodiments of this invention. For example, sample tray 30 can be made from an opaque material with holes so it is still possible to see the images on display panel 18. Sample containers may be directly placed on top of the display panel provided it is safe to do so, as discussed in DETAILED DESCRIPTION—FIG. 2 ALTERNATIVE EMBODIMENTS. The projector used in the alternative embodiment described in DETAILED DESCRIPTION—FIG. 3 ALTERNATIVE EMBODIMENTS can be any of the projectors including LCD, Super Video Graphics Array (SVGA) projectors, and laser projection display (LPD) projectors. For the handling of liquid samples, instructions such as transfer volume may be directly sent from the computer to an electronic pipette via wired or wireless communication. A plurality of computers and a plurality of display panels can be integrated into a single sample handling system. Sample handling control menu 20 can be either displayed on the same panel as the sample container image 26 or on a separated display panel. Positioning feature 32 and alignment feature 28 can be either permanently or temporally fixed to sample tray 30, or their positions can be made adjustable. In addition, an image on the display panel can be extended through optical means, such as fiber optics, to beyond the reach of the display panel 18.

Thus the scope of the invention should be determined by the appended claims and their legal equivalents, rather than by the examples given.

I claim:

1. A device for guiding sample handling, comprising:
   a. a computer,
   b. at least one image generation apparatus connected to said computer,
   c. a plurality of sample compartments, d. means for generating images representing said sample compartments by said image generation apparatus through computer software, e. means for aligning said sample compartments with said image generation apparatus, whereby a user can conveniently associate said images with said compartments and identify or locate said sample compartments during a sample handling process.

2. The device of claim 1 wherein, further comprising:

a. a rigid structure having sufficient size to accommodate placement of a plurality of sample compartments, b. means for permitting visual observation of said images through said structure.

3. The device of claim 2 wherein said rigid structure is made of transparent material.

4. The device of claim 2 wherein said rigid structure has holes.

5. The device of claim 1 wherein said image generation apparatus is selected from the group consisting of liquid crystal display flat panel computer monitors, cathode ray tube computer monitors, plasma television monitors, digital light processor projectors, and liquid crystal display projectors.

6. The device of claim 1 wherein said sample compartments are in array formats and are subunits of sample containers.

7. The device of claim 1 wherein, further comprising means for signaling actions to be taken on said sample compartments through changes of said images.

8. The device of claim 7 wherein said changes are selected from the group consisting of changing color, changing size, changing shape, changing flashing rate, changing intensity, changing pattern, linking said images, pointing to or away from said images using arrows, and highlighting area surrounding said images.

9. The device of claim 1 wherein further comprising an input device for said computer to select said images, whereby a user can conveniently record desired sample properties by selecting said images which are correspondent to said sample compartments housing the samples with desired properties visually observed.

10. The device of claim 9 wherein further comprising a text input device for said computer to accept user entered text data, whereby a user can record sample properties by selecting said images which are correspondent to said sample compartments housing the samples and then enter the visually observed properties through said text input device.

11. A device for guiding sample handling, comprising:

a. a computer, b. at least one image generation apparatus connected to said computer, c. a plurality of sample compartments, d. means for generating images representing said sample compartments by said image generation apparatus through computer software, e. means for transmitting said images to said sample compartments, whereby a user can conveniently associate said images with said compartments and identify or locate said sample compartments during a sample handling process.

12. The device of claim 11 wherein said means is selected from the group consisting of light transmitting by fiber optics, by optical mirrors, and by lenses.

* * * * *